(12) United States Patent
Hara et al.

(10) Patent No.: US 6,638,559 B1
(45) Date of Patent: Oct. 28, 2003

(54) ACTIVATION METHOD OF A STARCH DECOMPOSITION ENZYME IN FOOD MATERIAL

(75) Inventors: Yasuo Hara, Shimane-ken (JP); Akemi Katou, Shimane-ken (JP); Rieko Onishi, Matsue (JP); Eiko Arai, Tokyo-to (JP)

(73) Assignee: Hoshizaki Denki Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 09/593,420

(22) Filed: Jun. 14, 2000

(30) Foreign Application Priority Data

Dec. 10, 1999 (JP) ............................................. 11-352248

(51) Int. Cl.⁷ ................................................. A23L 1/10
(52) U.S. Cl. ...................................................... 426/626
(58) Field of Search .............................. 426/49, 18, 28, 426/74, 93, 309, 310, 331, 335, 532, 544, 629, 615, 521, 626

(56) References Cited

U.S. PATENT DOCUMENTS 5,928,491 A * 7/1999 Yu et al. ...................... 205/703

FOREIGN PATENT DOCUMENTS

JP  07 289 178  * 7/1995

OTHER PUBLICATIONS

Database Chemabs Online, Chemical Abstracts Service, Columbus Ohio, Kobayashi Kenji et al, "Solubility of Steamed Rice is Dependent on Electrolyzed Water," XP002162398, abstract, Nippon Jozo Kyokai, vol. 94, No. 11, 1999, pp. 926–932, Japan.
Database WPI, Section Ch., Week 199630; Derwent Publications Ltd., London, GB; Class D13, AN 1996–294578, XP002162399 & JP 08 126483 A (Nippon Seifun KK), May 21, 1996, abstract.
Abstract of Japanese Publication No. 11009254; dated Jan. 19, 1999.
Abstract of Japanese Publication No. 11137162; dated May 25, 1999.
Abstract of Japanese Publication No. 08131065; dated May 28, 1996.
Abstract of Japanese Publication No. 10151460; dated Jun. 9, 1998.
Abstract of Japanese Publication No. 11075810; dated Mar. 23, 1999.

* cited by examiner

*Primary Examiner*—Keith Hendricks
(74) *Attorney, Agent, or Firm*—Arent Fox Kintner Plotkin & Kahn, PLLC

(57) ABSTRACT

An activation method of decomposition enzyme contained in a food material, wherein the food material is brought into contact with electrolyzed water to activate the decomposition enzyme thereby to enhance taste of processed foodstuffs.

10 Claims, 4 Drawing Sheets

ACTIVATION METHOD OF A STARCH DECOMPOSITION ENZYME IN FOOD MATERIAL

BACKGROUND OF THE INVENTION

1. Field of the Invention

The present invention relates to a method of promoting the activity of decomposition enzyme in food materials.

2. Description of the Prior Art

There are various kinds of food materials containing various kinds of decomposition enzyme for decomposing ingredients included therein. For example, a lot of amylase in the form of starch decomposition enzyme is contained as a main component in grains such as rice, barley and the like or potato containing starch as a main component, and a lot of protease in the form of protein decomposition enzyme is contained as a main component in grains such as barley, beans and the like. Furthermore, a lot of lipase in the form of oil and fat decomposition enzyme is contained as a main component in beans, seafood, beast meat, bird meat, domestic animal meat and the like.

In the case that a food material processed in a raw condition is provided as raw foodstuff or a food material cooked by heating process is provided as heat-processed foodstuffs, decomposition enzyme in the food materials decomposes ingredients of the food materials and effects to add taste or flavor to the processed foodstuffs.

For example, in the case that a food material containing a lot of starch is subjected to a water addition process or a kneading process in a raw condition or subjected to a heating process, a lot of fresh water such as city water is used for processing the food material In such a processing, starch in the food material is decomposed by amylase contained in the food material to produce monosaccharide or oligosaccharide. The monosaccharide or oligosaccharide is a sweetness ingredient which effects to add flavor to the raw foodstuffs or the heat-processed foodstuffs.

Similarly, in the case that foodstuffs such as barley, beans or the like containing a lot of protein are processed by heat, the protein is decomposed by protease in the form of protein decomposition enzyme. In the case that foodstuffs such as various beans, meats, sea foods or the like containing a lot of oil and fat component are processed in a raw condition or processed by heat, the oil and fat are decomposed by lipase in the form of oil-fat decomposition enzyme to add flavor to the foodstuff.

It is, therefore, presumed that activation of decomposition enzyme in the food materials is useful to increase the taste or flavor of the foodstuffs processed in a raw condition or processed by heat. As a method of promoting the activity of the decomposition enzyme in the food materials, there have been proposed a method of adjusting pH of water used for processing the food materials in an extent of 5–6 pH, a method of increasing the concentration of metal ion such as calcium ion, magnesium ion, manganese ion and the like in the water used for processing the food materials, and a method of retaining the food materials added with water for a predetermine time at 40° C.–60° C. before processing the food materials. These methods are effective to activate the decomposition enzyme in the food materials in an optimal condition.

In the method of adjusting pH of the water used for processing of the food materials in a range of 5–6 pH an adjusting agent of pH is added to the water used for processing the food materials. Addition of the adjusting agent causes difficulty to adjust the pH of water to a predetermined value prior to each processing of the food materials. It is also required to carefully select the pH adjusting agent and determine an amount of the pH adjusting agent from a viewpoint of health.

In the method of increasing the concentration of various ions in the water used for processing the food materials, it is required to precisely measure an amount of metal compound for addition to the water prior to each processing of the food materials for adjusting the concentration of the metal ions to an optimal value. Although lactic acid calcium, calcium chloride, magnesium chloride, manganese chloride and the like can be used as the metal compound, the taste of the processed foodstuffs is deteriorated if the amount of the metal compound is excessive, and the decomposition enzyme may not be sufficiently activated if the amount of the metal compound is too small.

SUMMARY OF THE INVENTION

It is, therefore, a primary object of the present invention to provide a method of promoting the activity of decomposition enzyme in food materials without using any pH adjuster for adjustment of the pH of water used for processing the food materials or without adding any metal compound for adjustment of the concentration of the metal ions.

According to the present invention, the object is accomplished by a method of promoting the activity of decomposition enzyme contained in a food material, wherein the food material is brought into contact with electrolyzed water to activate the decomposition enzyme.

In the activation method, it is preferable that electrolyzed acid water or alkaline water is used as the electrolyzed water, and the food material is retained in an amount of the electrolyzed acid water or alkaline water at a predetermined temperature for a predetermined time. In the case that the food material is wheat, it is preferable that the wheat is retained in an amount of electrolyzed acid water at the predetermined temperature for the predetermined time. In the case that the food material is rice, it is preferable that the rice is retained in an amount of electrolyzed acid water at a temperature range of 30° C. to 50° C.

BRIEF DESCRIPTION OF THE DRAWINGS

Other objects, features and advantages of the present invention will be more readily appreciated from the following detailed description of a preferred embodiment thereof when taken together with the accompanying drawings, in which.

DESCRIPTION OF THE PREFERRED EMBODIMENT

Figure 1:
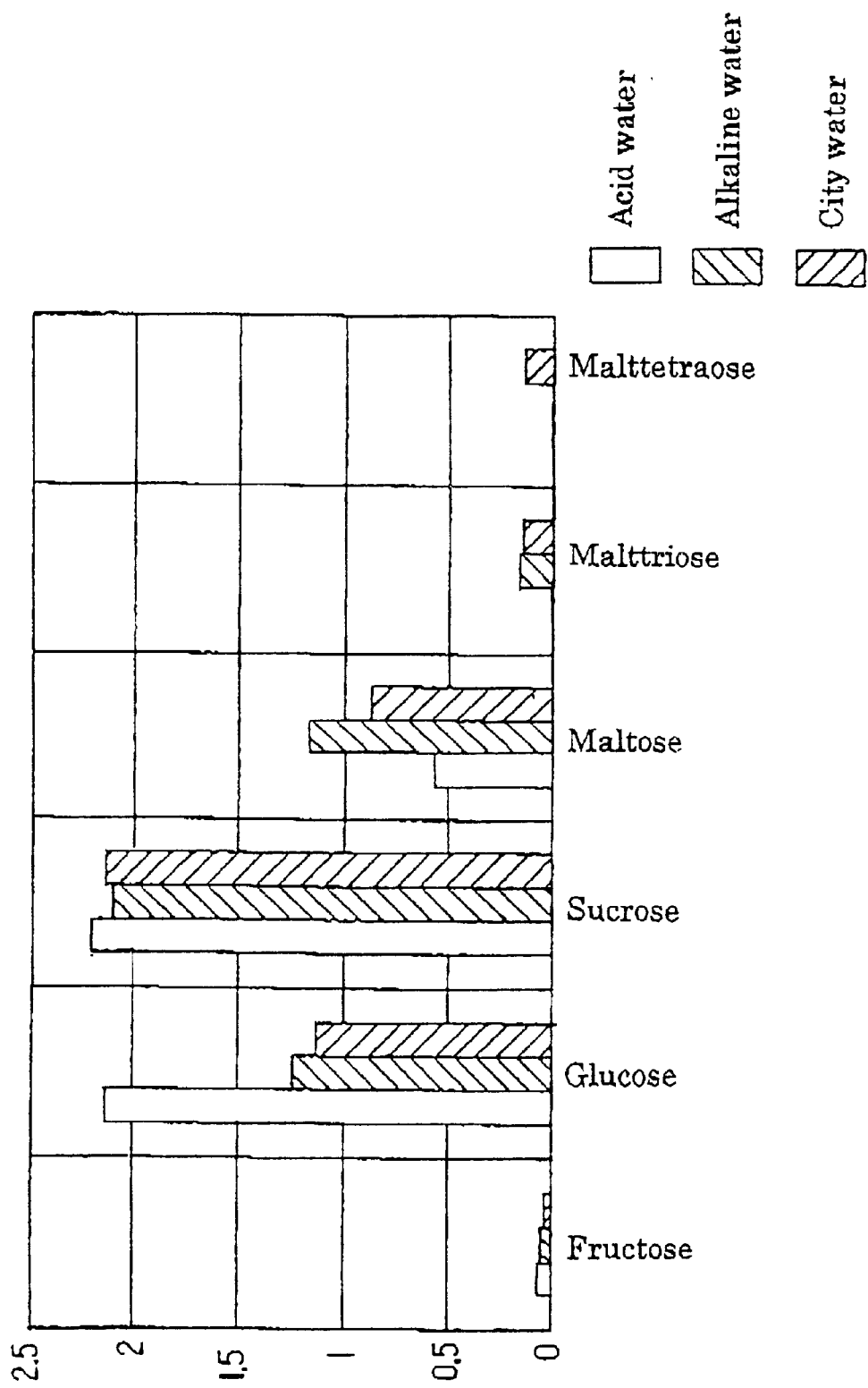
FIG. 1 is a graph showing each amount of saccharine components dissolved from rice powder in water treatment based on an activation method according to the present invention.

Hereinafter, a preferred embodiment of a method of promoting the activity of decomposition enzyme in accordance with the present invention will be described. In the activation method, a food material containing starch is retained in an amount of electrolyzed water at a predetermined temperature for a predetermined time to activate a starch decomposition enzyme for cooking the food material by heat.

The food material used in the activation method is selected from various kinds of food materials such as grains, potatoes and the like containing a lot of starch, and electrolyzed acid water of alkaline water is used as the electrolyzed water for water treatment of the food materials. Preferably, acid water of about 3.0–5.0 pH or alkaline water of about 8.0–10.0 pH is used for water treatment of the food materials. The acid water is produced in an anode chamber of an electrolyzed, while the alkaline water is produced in a cathode chamber of the electrolyzed. For production of the electrolyzed water, normal city service water or diluted brine is used as a raw water supplied into the electrolyzed. The food materials are retained in the electrolyzed water for a predetermined time to activate starch decomposition enzyme contained therein.

In use of the electrolyzed acid water for the processing method, it is desirable that the pH of acid water is determined to be about 3.0 to 5.0 pH. When the electrolyzed acid water is brought into contact with the food materials, the activity of starch decomposition enzyme contained in the food materials is promoted, and the pH of acid water becomes 5.0 to 6.0 pH. In the use of the electrolyzed alkaline water for the processing method, it is desirable that the pH of alkaline water is determined to be about 8.0 to 10.0 pH. During the production process of the electrolyzed alkaline water, the concentration of metal ions such as calcium ion, magnesium ion, manganese ion or the like increases in an extent of 20% to 30% more than those in the raw water used in the electrolyzed. The concentration of metal ion in the extent is useful to promote the activity of starch decomposition enzyme contained in the food materials.

During the processing method, the temperature of electrolyzed water is maintained in an extent of 20° C. to 70° C. to promote the activity of the starch decomposition enzyme. The promotion effect of the activity of starch decomposition enzyme at the temperature is added to the activity promotion effect caused by the activity of the electrolyzed water or metal ions in the electrolyzed water. As a result of the promotion of the activity of starch decomposition enzyme, a portion of starch in the food materials is decomposed by the enzyme to produce monosaccharide or oligosaccharide whose sweetness ingredient effects to add flavor to heat-processed foodstuff.

EXAMPLE 1

In this example, an appropriate amount of powder (of 300 μm in particle diameter) of old rice harvested in Shimane-ken, Japan and stored for on year) was used as a food material containing starch for an experimental water treatment. In the water treatment, city service water of 6.95 pH, acid water of 3.75 pH and alkaline water of 9.25 pH were used. The acid water and alkaline water were produced by an electrolyzed water production apparatus of HOX-40A type (made by Hoshizaki Denki K.K) using service water of Matsue-shi. In the water treatment, the rice powder was added with the water ten times the weight of rice powder and shaken for two hours at a water temperature of 25° C.

Each pH value of the water before and after the water treatment is listed in the following table 1, and each amount of soluble entire sugar and reducing sugar extracted from the lice powder is listed in the following table 2. In addition, each amount of the extracted sugar components is shown in a graph of FIG. 1. Provided that the soluble sugar extracted from the rice powder was measured by a phenol-sulfuric acid process, the reducing sugar was measured by Somogyi-Nelson method, and each amount of the sugars was measured by HPLC.

TABLE 1

| [pH of water before and after water treatment] | | | |
|---|---|---|---|
| Water | Acid water | Alkaline water | City water |
| Before treatment | 3.75 | 9.25 | 6.95 |
| After treatment | 5.63 | 7.91 | 6.77 |

TABLE 2

| [Extraction of sugar components from rice powder] | | | |
|---|---|---|---|
| Extracted component | Acid water (3.75) | Alkaline water (9.25) | City water (6.95) |
| Entire sugar | 14.2 | 13.4 | 12.5 |
| Reducing sugar | 3.36 | 3.10 | 2.49 |

From the table 1, the following facts have been found. In the case that the water used for the treatment of the rice powder is the electrolyzed acid water or alkaline water, the pH of the acid water becomes 5.63 most suitable for promoting the activity of starch decomposition enzyme, and the pH of the alkaline water becomes 7.91 most suitable for causing the metal ions such as calcium ion, magnesium ion, manganese ion and the like to promote the activity of starch decomposition enzyme. This means that the rice powder can be cooked by beat at lower or higher pH than that of the city water. The table 2 also indicates the facts that the extracted amount of soluble entire sugar and reducing sugar in use of the acid water or alkaline water increases more than that in use of the city water and that the extracted amount of the sugars in use of the acid water increases more than that in use of the alkaline water.

Referring to the graph of FIG. 1 as to the sugar components dissolved from the rice powder, any significant difference in each amount of fructose and sucrose was not found in use of the electrolyzed water and city water, but an amount of glucose dissolved in use of the acid water was more than that in use of the city water whereas an amount of maltose in use of the acid water was less than that in use of the city water. It has been also found that each amount of glucose and maltose dissolved in use of the alkaline water was more than that in use of the city water.

From the foregoing facts, it is presumed that the amount of the sugar components extracted in use of the acid water or alkaline water is increased by the fact that each amount of glucose and maltose extracted from the rice powder respectively in the acid water and alkaline water is increased by the function of starch decomposition enzyme contained in the rice powder.

At pages 29–34 of a publication "Starch Science Vol. 37, No. 1, (1990)", Maruyama et al. reported that two kdnds of α-amylase are contained in rice and that the decomposition function of α-amylase becomes most effective in an extent of 5 pH to 6 pH. During the water treatment using the acid water, the pH of electrolyzed water becomes an optimal value suitable for promoting the activity of α-amylase. It is, therefore, presumed that the activity of starch decomposition enzyme is promoted by the pH effect. Since in use of the acid water, the extracted amount of glucose is increased whereas the extracted amount of maltose is decreased, it is presumed that the activity of α-glucosidase is promoted to enhance the activity of starch decomposition enzyme.

In use of the alkaline water, the extracted amount of glucose and maltose is increased in spite of lower pH than the optimal value effective for the decomposition function of α-amylase. In this respect, it has been confirmed by Maruyame et al. that the two kinds of α-amylase are activated by calcium ion, magnesium ion, manganese ion and the like. Accordingly, it is presumed that in the water treatment using the alkaline water, the activity of α-amylase is promoted by an increase of cation transferred to the cathode from the anode in the course of production of the alkaline water.

From the foregoing facts, it is presumed that the activity of starch decomposition enzyme is promoted by the pH effect or ion effect when the acid water alkaline water is used for water treatment of food materials such as rice containing starch. With promotion of the activity of starch decomposition enzyme, starchiness and swelling of the starch are promoted by heat cooking.

EXAMPLE 2

Figure 2:
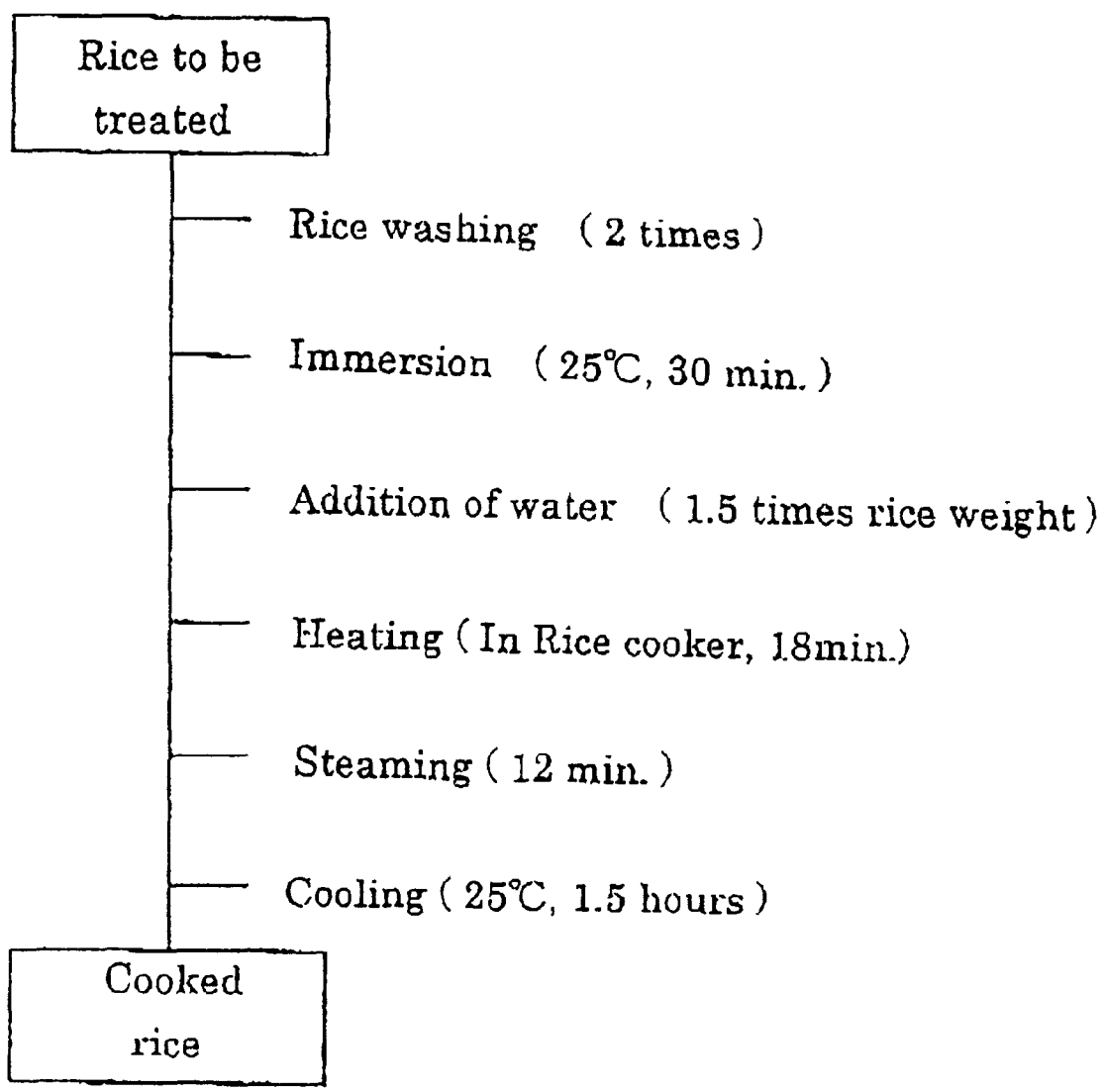
FIG. 2 is a view showing a rice cooking process based on an activation method according to the present invention.

In this example, city water of 6.95 pH, acid water of 3.75 pH and alkaline water of 9.25 pH were used to cook an appropriate amount of old rice stored for one year by a cooking process shown in FIG. 2. Provided that, the rice and water were the same as those used in the Example 1.

As shown in FIG. 2, the rice cooking process comprises the steps of rice washing, immersing the washed rice in the water, adding the water to the immersed rice after draining, heating the immersed rice, steaming the boiled rice, and cooling the steamed rice. During the rice cooking process, the nice was washed with the water two times the weight of rice and drained. After drained, the washed rice was added with fresh water and immersed in the fresh water at 25° C. for thirty minutes. Thereafter, the immersed rice was drained and added with fresh water 1.5 times the weight of rice. Thus, the rice immersed in the fresh water was heated in an electric rice cooker for eighteen minutes and subsequently steamed for twelve minutes. Finally the cooked rice was cooled at 25° C. for one and half hours. A change of pH of the used water at each step of the rice cooking process is show in the following table 3.

TABLE 3

[pH of the used water at each step of the rice cooking process]

| Process step | Acid water | Alkaline water | City water |
|---|---|---|---|
| After washing | 6.23 | 7.46 | 6.79 |
| After Immersion | 6.11 | 7.06 | 6.68 |
| After addition of fresh water | 5.63 | 7.91 | 6.77 |

From the table 3, it has been found that the pH of electrolyzed acid water and alkaline water used for the rice cooking becomes approximately neutral at the step of rice washing and immersion in the fresh water and becomes more acid and alkaline than the city water at the water addition step. This means that the rice immersed in the acid water or alkaline water is cooked by heat at lower pH or higher pH than that immersed in the city water.

Sensual Evaluation

As to the rice cooked by the rice cooking process shown in FIG. 2, a sensual evaluation was conducted by a consumer's panel of twenty person. The evaluation was made as to six properties such as color, glossiness, hardness, stickiness, taste and synthesis evaluation, and the rice cooked with the city water was evaluated as a standard value "0" in an evaluation extent of +3 to −3. A result of the evaluation is shown in a graph of FIG. 3, in which a solid lie indicates the rice cooked with the acid water, a broken line indicates the rice cooked with the alkaline water, and a dot-and-dash line indicates the rice cooked with the city water.

Figure 3:
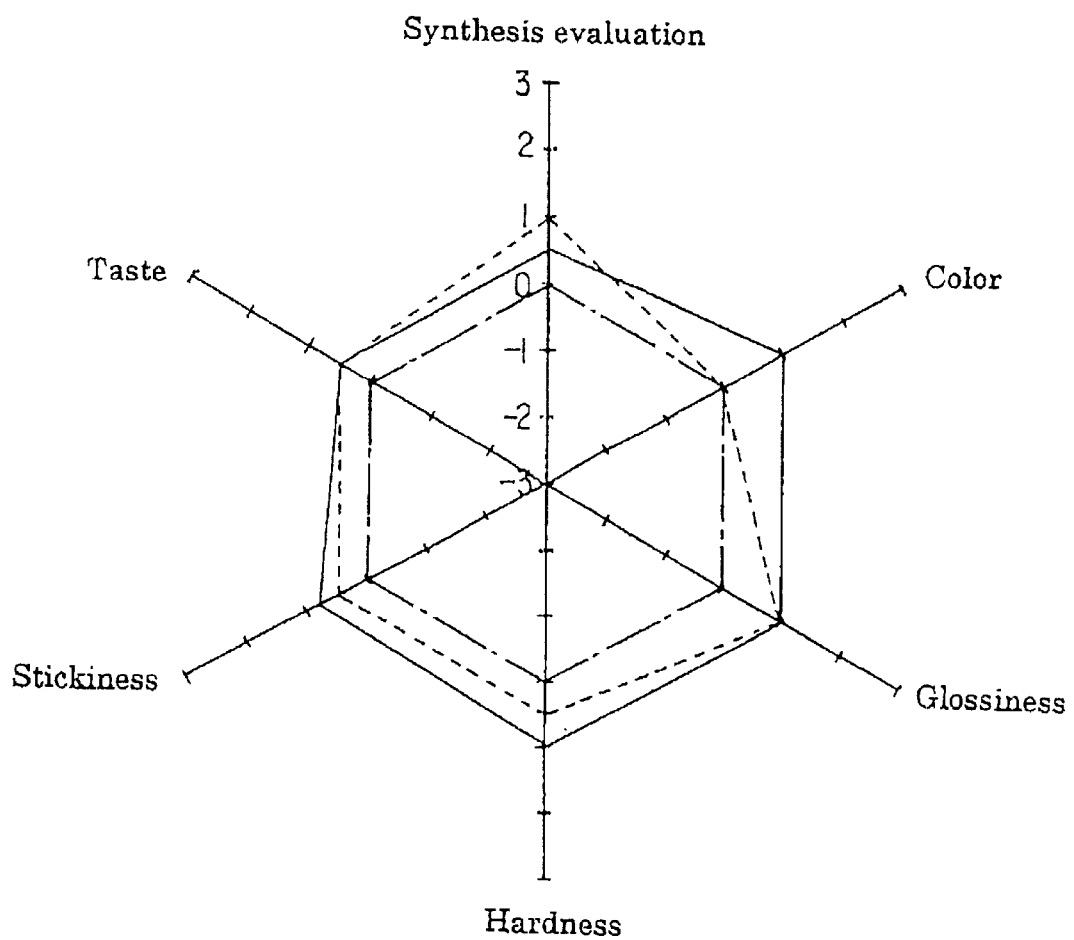
FIG. 3 is a graph showing a sensual evaluation of cooked rice.

From the graph of FIG. 3, it has been found that the rice cooked with the acid water or alkaline water is more glossy, soft, sticky and tasty than the rice cooked with the city water and is also superior in synthesis evaluation. It is been also found that the rice cooked with the acid water is superior particularly in color more than the rice cooked with the alkaline water or the city water.

From the results described above, it has been confirmed that the old rice cooked with the acid water or line water is superior in sensual property than the rice cooked with the city water.

Texture of Cooked Rice

The texture or property of each rice cooked with the electrolyzed water and city water was measured by a three-grains method, and the starchiness degree of each rice was measured by a BAP method. A result of the measurement is shown in the following table 4.

TABLE 4

[Property of cooked rice]

| Texture | Acid water (3.75) | Alkaline water (9.25) | City water (6.96) |
|---|---|---|---|
| Hardness (kg) | 3.24 | 2.30 | 2.47 |
| Stickiness (kg) | 0.31 | 0.34 | 0.28 |
| Stickiness/Hardness | 0.14 | 0.14 | 0.12 |
| Starchiness degree (%) | 95.3 | 96.5 | 92.2 |

As is shown in the table 4, the hardness of the rice cooked with the acid water or alkaline water was decreased and the stickiness of the rice was increased. In addition, tie starchiness and swelling of starch was promoted. From these facts, it has been found that the texture or property of the rice cooked with the acid water or the alkaline water is improved in comparison with the rice cooked with the city water.

To further compare with the texture of the rice cooked with the city water, the rice cook with the acid water or alkaline water was frozen and dried immediately after cooking, and the cross-section of the dried rice was observed by SEM. In this observation, a number of large holes dispersed entirely in the rice cooked with the city water were found. These holes are seemed to be traces caused by starch dehydrated at the freezing and drying processes. In contrast with the rice cooked with the city water, these holes formed in the rice cooked with the alkaline water were rather small than those in the rice cooked with the city water, and these holes formed in the rice cooked with the acid water were rather small than those in the rice cooked with the alkaline water.

From the foregoing facts, it is presumed that a hydrated condition of starch in the rice cooked with the acid water or alkaline water is enhanced in contrast with the rice cooked with the city water. It is also presumed that the hydrated condition or starch in the rice cooked with the acid water is noticeably enhanced in contrast with the rice cooked with the city water.

EXAMPLE 3

In this example, an appropriate amount of wheat flour (produced by Nissin Seifun K.K. and named "Super Cameria) was used as a food material containing an amount of starch for an experimental water treatment. In the water treatment, city water of 6.95 pH and acidic water of 3.5 pH were used. The city water was service water of Matsue-shi, and the acid water was produced by the electrolyzed water production apparatus of HOX-40A type (made by Hoshizaki Denki KK) using the service water of Matsue-shi.

In the experimental water treatment wheat flour of 0.2 g was added with the water of 20 ml (100 times the wheat flour) and shaken for ninety minutes at a water temperature of 30° C. The treated water was filtered by a filter of 0.45 μm, and the top clear part of the filtered water was obtained for the following measurement Thus, the pH of the treated water before and after the water treatment was measured. Additionally, the entire amount of sugar components contained in the top clear part of the filtered water was measured by a phenol-sulfate method and an amount of reducing sugar was measured by Somogyi-Nelson method A result of the measurement of pH is listed in the following table 5, and a result of the measurement of sugar components is listed in the following table 6.

TABLE 5

[pH of treated water]

| Treated water | Acid water | City water |
| --- | --- | --- |
| Before treatment | 3.5 | 6.9 |
| After treatment | 5.6 | 6.1 |

TABLE 6

[Sugar components extracted from wheat flour]

| Extracted components | Acid water | City water |
| --- | --- | --- |
| Entire sugar | 60.6 | 57.0 |
| Reducing sugar | 10.5 | 4.9 |

From the results of the measurement described above, it has been found that the amount of entire sugar and reducing sugar extracted from the acid water becomes more than that extracted from the city water. This means that the activity of α-amylase is enhanced in the acid water.

In preparation of wheat flour products, city water or natural water is used in general to prepare batter or dough, and sweetness of the wheat flour products are given by not only sugar added in preparation of the batter or dough but also decomposition of starch contained in wheat flour. The starch is decomposed by molecularity thereof and α-amylase contained therein. Since more than seventy percent of flour components are decomposed into sugar components, the decomposition of starch is very important for preparation of the wheat flour products. For this reason, if the electrolyzed acid water was used for preparation of wheat flour products, α-amylase would be effectively activated to promote decomposition of starch contained in wheat flour and to enhance sweetness of the wheat flour products.

EXAMPLE 4

In this example, an amount of powder (of 100 μm in particle diameter) of old rice (store for one year) was subjected to an experimental water treatment using electrolyzed acid water of 3.65 pH and city water of 6.95 pH. The water treatment of the rice powder was conducted at a water temperature of 10° C.–70° C., and the same as in the example 3 was used for the water treatment.

In the water treatment, the rice powder of 0.2 g was added with the water of 20 ml (100 times the rice powder) and shaken for thirty minutes at a predetermined temperature. Subsequently, the water was filtered by a filter of 0.45 μm, and the top clear part of the filtered water was obtained for the following measurement. Thus, an amount of entire sugar components contained in the top clear part of the filtered water was measured by a phenol-sulfate method, and an amount of reducing sugar was measured by Somogyi-Nelson method. Based on a result of the measurement, the activity of α-amylase was calculated, and a result of the calculation is shown in the following table 7 and shown by the graph in FIG. 4. Provided that, activity of α-amylase was calculated by a formula "Reducing sugar/Entire sugar." In the graph of FIG. 4, a solid line indicates the acid water used in the water treatment, and a dot-and-dash line indicates the city water used in the water treatment.

TABLE 7

[Activity of α-amylase]

| Temperature (° C.) | Acid water (3.65) | City water (6.95) |
| --- | --- | --- |
| 10 | 0.18 | 0.06 |
| 30 | 0.23 | 0.12 |
| 40 | 0.49 | 0.28 |
| 50 | 0.27 | 0.10 |
| 70 | 0.18 | 0.07 |

Figure 4:
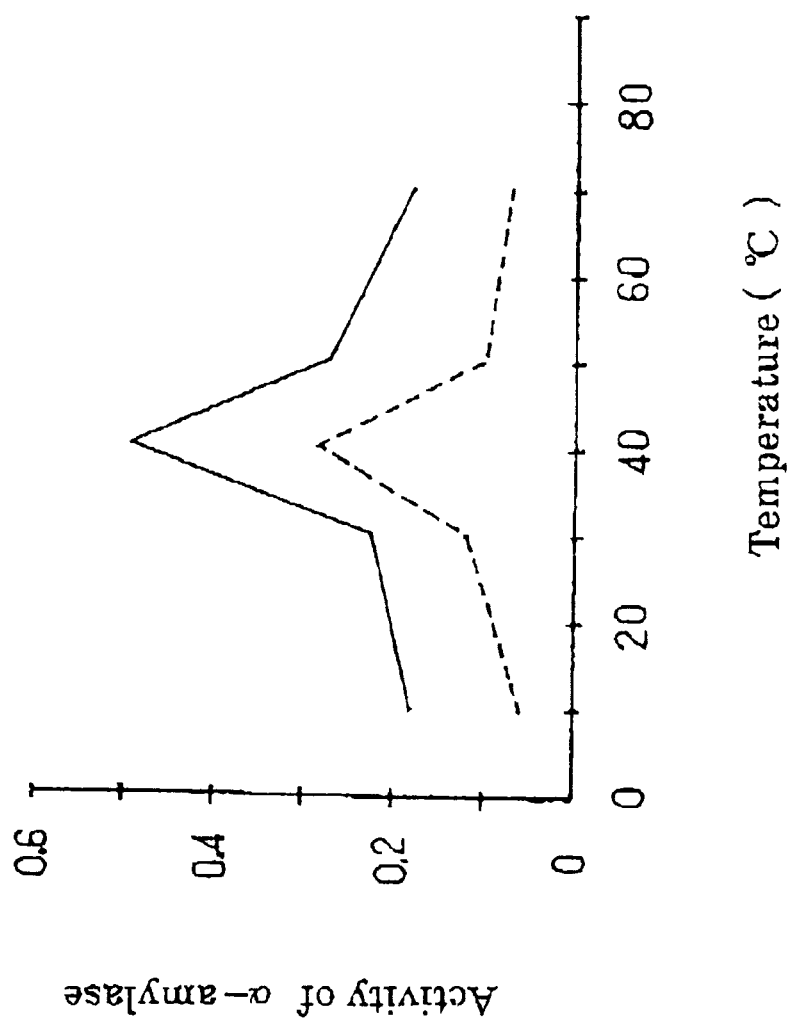
FIG. 4 is a graph showing an activation degree of α-amylase in relation to a temperature in water treatment of the rice powder.

From tie table 7 and graph of FIG. 4, it has been found that the activity of α-amylase in the treatment with the acid water becomes higher than that in the treatment with the city water at all the temperatures. Particularly, the activity of α-amylase becomes higher at the water temperatures of 30° C. and 50° C.

What is claimed is:

1. A method of promoting the activity of a starch decomposition enzyme in a food material containing starch, consisting essentially of the steps of:

preparing an amount of electrolyzed acid water of about 3.0 to 5.0 pH; and retaining the food material in the electrolyzed acid water at a predetermined temperature for a predetermined time during which the pH of the acid water becomes 5.0 to 6.0 without the use of any pH adjuster.

2. A method of promoting the activity of a starch decomposition enzyme in a food material containing starch, consisting essentially of the steps of:

preparing an amount of electrolyzed acid water of about 3.0 to 5.0 pH; and retaining the food material in the electrolyzed acid water at a temperature range of 20° C. to 70° C. for a predetermined time during which the pH of the acid water becomes 5.0 to 6.0.

3. A method of promoting the activity of the starch decomposition enzyme according to claim 2, wherein the food material is a vegetable food material.

4. A method of promoting the activity of a starch decomposition enzyme in wheat flour, comprising the steps of:

preparing an amount of electrolyzed acid water of about 3.0 to 5.0 pH; and retaining the wheat flour in the electrolyzed acid water at a predetermined temperature for a predetermined time during which the pH of the acid water becomes 5.0 to 6.0 without the use of any pH adjuster.

5. A method of promoting the activity of a starch decomposition enzyme in rice, comprising the steps of:

preparing an amount of electrolyzed acid water of about 3.0 to 5.0 pH; and retaining the rice in the electrolyzed acid water at a temperature range of 30° C. to 50° C. for a predetermined time during which the pH of the acid water becomes 5.0 to 6.0 without the use of any pH adjuster.

6. A method of promoting the activity of a starch decomposition enzyme in a food material containing starch, consisting essentially of the steps of:

preparing an amount of electrolyzed alkaline water of about 8.0 to 10.0 pH; and retaining the food material in the electrolyzed alkaline water at a predetermined temperature for a predetermined time during which the concentration of metal ions in the alkaline water increases in an extent of 20% to 30% more than those in a raw water for preparation of the electrolyzed alkaline water without the addition of any metal compound.

7. A method of promoting the activity of a starch decomposition enzyme in a food material containing starch, consisting essentially of the steps of:

preparing an amount of electrolyzed alkaline water of about 8.0 to 10.0 pH; and retaining the food material in the electrolyzed alkaline water at a temperature range of 20° C. to 70° C. for a predetermined time during which the concentration of metal ions in the alkaline water increases in an extent of 20% to 30% more than those in a raw water for preparation of the electrolyzed alkaline water.

8. A method of promoting the activity of the starch decomposition enzyme according to claim 7, wherein the food material is a vegetable food material.

9. A method of promoting the activity of a starch decomposition enzyme in wheat flour, comprising the steps of:

preparing an amount of electrolyzed alkaline water of about 8.0 to 10.0 pH; and retaining the wheat flour in the electrolyzed alkaline water at a predetermined temperature for a predetermined time during which the concentration of metal ions in the alkaline water increases in an extent of 20% to 30% more than those in a raw water for preparation of the electrolyzed alkaline water without the addition of any metal compound.

10. A method of promoting the activity of a starch decomposition enzyme in rice, comprising the steps of:

preparing an amount of electrolyzed alkaline water of about 8.0 to 10.0 pH; and retaining the rice in the electrolyzed alkaline water at a temperature range of 30° C. to 50° C. for a predetermined time during which the concentration of metal ions in the alkaline water increases in an extent of 20% to 30% more than those in a raw water for preparation of the electrolyzed alkaline water without the addition of any metal compound.

* * * * *